United States Patent [19]
Denker

[11] Patent Number: 6,099,460
[45] Date of Patent: Aug. 8, 2000

[54] ELECTROMAGNETIC HEART ASSIST TECHNIQUE AND APPARATUS

[76] Inventor: Stephen Denker, 2130 W. Columbia Dr., Mequon, Wis. 53092

[21] Appl. No.: 09/067,672

[22] Filed: Apr. 28, 1998

[51] Int. Cl.⁷ .................................................. A61M 1/12
[52] U.S. Cl. ................................ 600/17; 600/16; 600/12; 600/13; 600/14; 623/3.1
[58] Field of Search .................... 600/16–18, 12, 600/9, 13, 14; 623/3, 3.1, 3.11; 607/3

[56] References Cited

U.S. PATENT DOCUMENTS

| | | | |
|---|---|---|---|
| 3,949,757 | 4/1976 | Sabel | 128/404 |
| 4,176,411 | 12/1979 | Runge | 3/1.7 |
| 4,454,883 | 6/1984 | Fellus | 128/422 |
| 4,809,713 | 3/1989 | Grayzel | 128/785 |
| 5,170,784 | 12/1992 | Ramon et al. | 128/419 |
| 5,674,271 | 10/1997 | Denker | 607/119 |

*Primary Examiner*—Kennedy Schaetzle
*Attorney, Agent, or Firm*—Quarles & Brady LLP; George E. Haas

[57] ABSTRACT

A heart can be artificially contracted to pump blood by separate electromagnets to the exterior surface of the heart and implanting another electromagnet inside a heart chamber. Electric currents are selectively applied to the electromagnets thereby producing magnetic fields which attract the electromagnets. That attraction generates forces which contract chambers of the heart and pump blood from those chambers. A technique for generating an electric current from a natural contraction of the heart also is described.

31 Claims, 2 Drawing Sheets

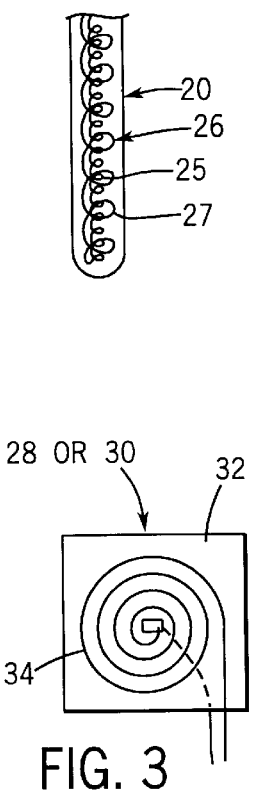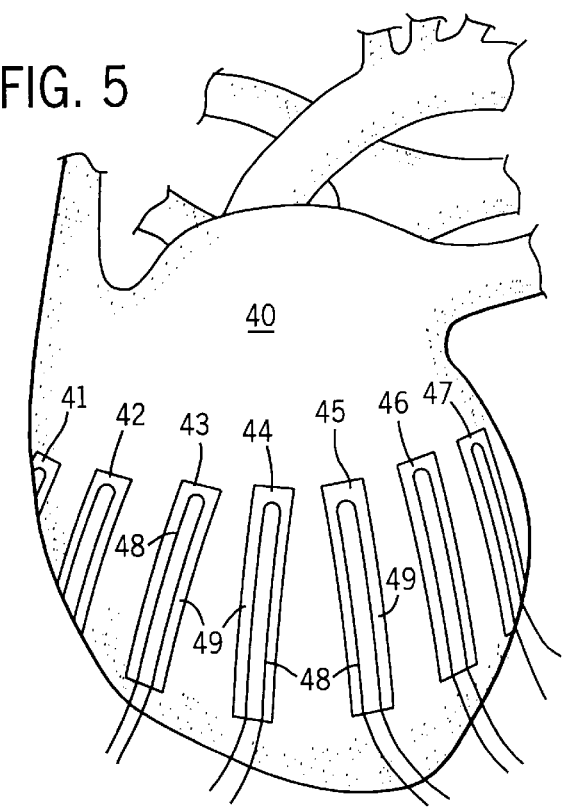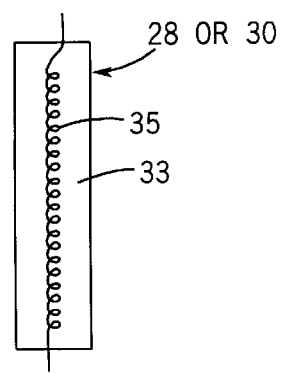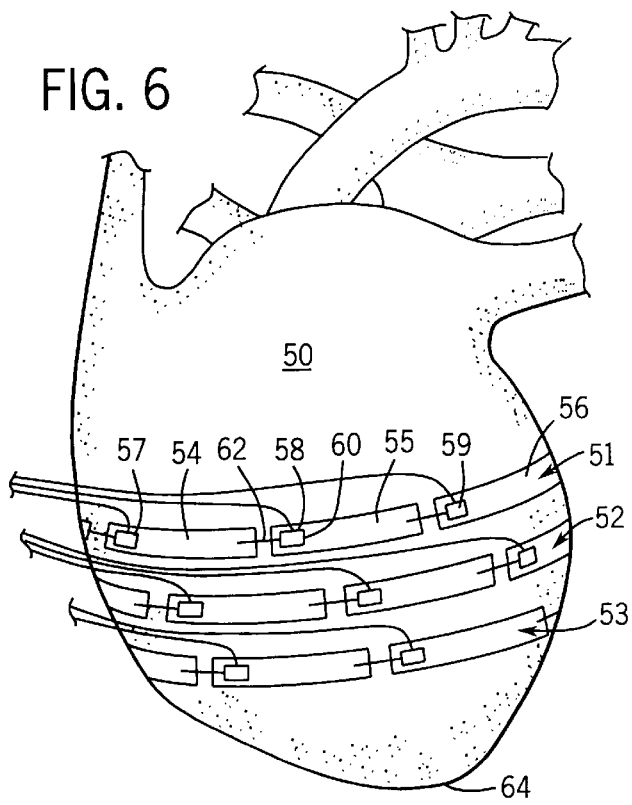

ELECTROMAGNETIC HEART ASSIST TECHNIQUE AND APPARATUS

BACKGROUND OF THE INVENTION

The present invention relates to artificial devices for assisting the pumping action of a heart.

Cardiac disorders often prevent the heart from being able to contract properly and pump blood through the arteries. One treatment involves surgically implanting an artificial pacing device with electrodes attached to the surface or inside of the heart. A controller of the implanted pacing device periodically sends electrical pulses to the electrodes which stimulate the heart muscle to contract and pump blood from the heart chambers. This pacing action controls the contraction of the heart thereby providing a natural pumping action of the blood.

Individuals with more severe cardiac disease may not be eligible for conventional pacing as the muscles of the heart have deteriorated so significantly that external stimulation will not produce sufficient pumping action. Treatment of these individuals may involve cutting away a portion of a ventricle of the heart and implanting an artificial pump in the opening. The artificial pump supplements the heart's pumping action. This radical solution often is the last option available for the patient, as it permanently removes part of the heart where the artificial pump is inserted. Typically this treatment is used only to prolong a person's life long enough to find a donor heart for transplantation.

Therefore, it is desirable to provide a technique for artificially inducing contraction of a heart in individuals with significant muscle deterioration, where the procedure is less invasive and less radical than the surgical implantation of an artificial pump.

SUMMARY OF THE INVENTION

A general object of the present invention is to provide a technique and apparatus for artificially contracting chambers of the heart to pump blood in situations where conventional cardiac pacing is insufficient. This invention enhances the cardiac output of the heart.

Another object of the present invention is to utilize electromagnets to produce magnetic fields which cause contraction of the heart chambers.

A further object of the present invention is to utilize a plurality of electromagnets and control the application of electric current individually to each one so as to produce a controlled contraction which optimizes the pumping of blood.

These and other objectives are satisfied by a method for artificially contracting the heart in an animal to pump blood. A first magnet is attached on one side of a first chamber of the heart, wherein the first magnet produces a first magnetic field. A second magnet is attached on another side of the first chamber, wherein the second magnet produces a second magnetic field. In the preferred embodiment of the present method, both of these magnets are electromagnet coils which produce a magnetic field when an electric current is sent through the coils.

To contract the heart, the first magnet is selectively activated to produce the first magnetic field which interacts with the second magnetic field. That interaction generates a force which contract the first chamber of the heart.

The present method can be used to contract either one or both of the right and left ventricles of the heart. In that case, it is preferred to attach separate electromagnet coils to the exterior surface of the heart outside both ventricles. Another coil on a catheter is inserted into one of the ventricles and secured to a wall of the heart. Pulses of electric current are applied to the different coils to produce magnetic fields which generate forces that attract the coils to each other and contract the right and left ventricles.

BRIEF DESCRIPTION OF THE DRAWINGS

FIG. 2 is a detailed representation of a catheter shown in FIG. 1;

FIG. 3 illustrates one of the external electromagnetic coils used in FIG. 1;

FIG. 4 illustrates an alternative embodiment of an external electromagnetic coil;

FIG. 5 shows human heart with electromagnetic coils applied for a second embodiment of the present invention;

FIG. 6 shows human heart with electromagnetic coils applied for a third embodiment of the present invention.

DETAILED DESCRIPTION OF THE INVENTION

Figure 1:
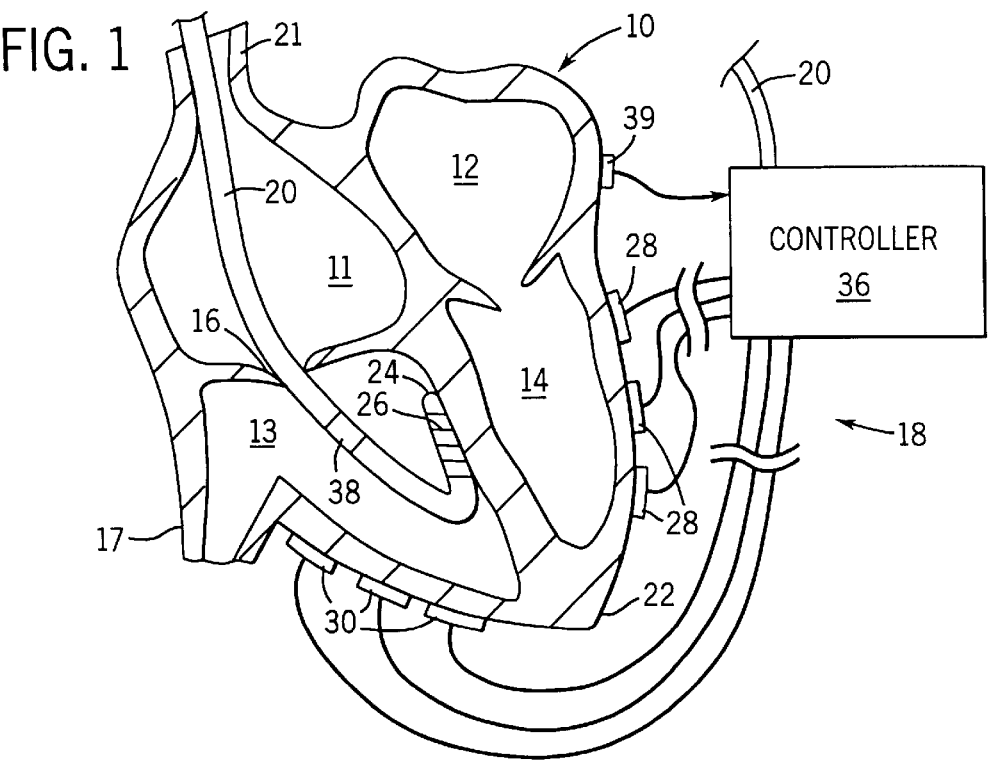
FIG. 1 is a cross-sectional view of a human heart to which the present technique is being applied.

With initial reference to FIG. 1, a human heart 10 has a right atrium 11, a left atrium 12, a right ventricle 13 and a left ventricle 14. Blood returning to the heart 10 from the body flows through the superior and inferior vena cava and passes into the right atrium 11 wherefrom it is pumped through the tricuspid valve 16 and into the right ventricle 13. Contraction of the right ventricle 13 causes the tricuspid valve 16 to close in response to the generated pressure and the blood to flow outward through the pulmonary arteries. After having passed through the lungs, oxygenated blood returns to the left atrium 12, where it is boosted into the left ventricle and thereafter pumped to the body through the aorta.

For hearts which are unable to pump an adequate amount of blood to the body, an artificial contraction assist device 18 is implanted into the patient. Using known procedures, a catheter 20 is introduced into any of several veins and advanced through the superior vena cava 21 into the right atrium 11. Further advancement causes the catheter 20 to pass through the tricuspid valve 16 and into the right ventricle 13. This procedure is similar to ones used in implanting catheters for conventional cardiac pacing devices. In those procedures, the catheter electrode tip ordinarily is wedged into the interior wall of the right ventricle pointing toward the apex 22.

The same general procedure may be followed to introduce the electromagnetic stimulation catheter 20 according to the present invention. That catheter 20 is preferably of a steerable type such as the one disclosed in U.S. Pat. No. 5,674,271. The catheter 20 has electrical wires running there through to tip 24 where the wires connect to a coil 26 wound in a spiral lengthwise along the catheter as shown in FIG. 2. Specifically, the coil 26 comprises an inner winding 25 and an outer winding 27 wound in the opposite direction coaxially around the inner winding. Because the inner and out windings 25 and 27 are wound in opposite directions, their individual electromagnetic fields add together. The steerable nature of the catheter 20 allows coil 26 to be placed against the septum between the two ventricles 13 and 14 as shown in FIG. 1. The tip 24 may include a corkscrew-like element for imbedding into the septum to secure the catheter in place. Alternatively, other techniques commonly utilized with pacing catheters may be employed to secure the catheter tip.

A plurality of electrical coils 28 are applied to the exterior surface of the heart outside the left ventricle 14. Another plurality of electrical coils 30 are applied to the exterior surface of the right ventricle 13. As shown in FIG. 3, each electrical coil 28 and 30 preferably comprise a flexible substrate 32 which is applied to the exterior surface of the heart 10 with surgical adhesive or stitches. An electrical spiral shaped coil 34 is on the substrate 32 and may be sandwiched between two layers of the substrate. The coil 34 can be formed by a wire that is wound in a spiral on the substrate surface or can be formed by a thin layer of electrically conductive material that has been etched to form the spiral pattern. Electrical wires are connected to each end of the coil 34. Alternatively, the coils for one side of the heart could be formed on a single flexible substrate.

Other forms of electrical coils can be utilized with the present heart assistance technique. For example as depicted in FIG. 4, the external coils 28 and 20 may be formed by an elongated spiral winding 35 carried by a strip-like flexible substrate 32. The flexible substrate 32 is applied in a generally vertical orientation to the exterior surface of the heart 10 and held in place with surgical adhesive or stitches.

The wires in the catheter 20 and from the electrical coils 28 and 30 extend to a controller 36. This controller is similar to prior cardiac pacing devices which produce electrical pulses applied to electrodes that stimulate a responsive contraction of the heart muscles. However, the present controller 36 applies pulses of electric current through the various coils to generate magnetic fields that cause the coils to be attracted to each other in a controlled manner. Specifically, when a contraction of the ventricles 13 and 14 is desired, the controller 36 applies an electrical pulse of direct current, having a duration equal to that of the desired contraction, to the coil 26 of catheter 20. During that catheter pulse, pulses of direct current also are applied to the external electrical coils 28 and 30. The electric currents applied to the catheter coil 26 and the external electric coils 28 and 30 produce electromagnetic fields about those coils. Due to the direction of the direct current through each coil, the magnetic fields are polarized so that the external coils 28 and 30 are attracted toward the internal coil 26 of catheter 20. This magnetic attraction contracts the right and/or left ventricles 13 and 14 in much the same manner as though the heart muscles contracted the ventricles.

Typically the controller also receives an input signal from a plurality of sensors, collectively represented by sensor 39, which indicate when a natural contraction of the heart is occurring. The controller 36 responds to that signal by applying electrical pulses to the coils 26, 28 and 30. Usually the patient has some cardiac function which is a fraction (e.g. 50%) of the normal function. In this case the electrical pulses will be timed and applied at the end of the natural heart contraction to compress the ventricles the remaining amount to achieve full cardiac output. Thus the present technique increases the efficiency of a defective heart.

The controller can be programmed so that the external coils 28 and 30 for each ventricle 14 and 13 are pulsed separately or simultaneously. The magnitude of electrical current applied to each coil 26, 28 and 30 can be regulated independently to produce the desired amount of heart contraction of each ventricle 13 and 14. For example, the controller 36 can vary the current magnitudes in response to sensing the pressure in the right ventricle by means of a pressure sensor 38 positioned on the catheter 20. The external coils 28 and 30 for a given ventricle may be pulsed in unison or sequentially pulsed by the controller 36 to squeeze the ventricle in a progressive manner from the apex 22 to the base or outflow area to force the blood from the ventricle through the aorta.

With reference to FIG. 5, an alternative implementation of the present invention utilizes a plurality of external electromagnet coils 41, 42, 43, 44, 45, 46 and 47 with additional coils similarly positioned on the rear side of the heart 40. This embodiment eliminates the need for a catheter with a coil inside the heart. Each external electromagnet coil 41–47 comprises at least one loop 48 of an electrical conductor attached to a flexible substrate 49 which is applied to the exterior surface of the heart 40 with surgical adhesive or stitches.

To contract the heart 40, electric current is applied in opposite directions through adjacent coils 41–47. For example, the electric current may flow in the clockwise direction through the odd numbered coils 41, 43, 45 and 47 and flow counter-clockwise in the even numbered coils 42, 44 and 46. This produces oppositely poled electromagnetic fields in adjacent coils resulting in forces which cause attraction of the adjacent coils. As the coils come toward each other the exterior wall of the heart 40 becomes pleated thereby contracting the ventricles. Similar electromagnet coils may be applied to the upper portion of the heart to assist contraction of the atria.

Referring to FIG. 6, a third embodiment of the present cardiac assistance technique applies a plurality of external bands 51, 52 and 53 around the ventricular region of the heart 50. Each band 51–53 is formed by a series of segments coupled having ends coupled together by electromagnetic actuators. For example, the first band 51 has segments 54, 55 and 56 with other segments extending around the rear of the heart 50. Each actuator 57, 58 and 59 of the first band 51 comprises a solenoid coil attached to one segment of the band with an armature connected to another segment. For example, actuator 58 has a solenoid coil 60 connected to band segment 55 and an armature 62 coupled to band segment 54. The bands 51–53 may have various numbers of segments and corresponding numbers of actuators. At the very least a band has a single segment with one actuator coupling the ends of that segment together. In addition the number of bands applied to the heart may vary.

To produce contraction of the ventricles of the heart 50, the controller applies electric current simultaneously to all of the actuators of a given band 51–53. For the first band 51 actuators 57, 58 and 59 will be energized simultaneously. This action creates electromagnetic fields which draw the armatures into the solenoid coils of the actuators 57–59, thereby pulling the band segments 54–56 closer together. Thus the perimeter of the band 51 is reduced, contracting the heart 50. The other bands 52 and 53 may be contracted at the same time as the first band 51 or the bands may be energized sequentially starting with the band 53 closest to the apex 64. This latter action produces a progressive contraction of the heart 50 toward the outflow area to force the blood from the ventricle through the aorta.

The present invention utilizes the electromagnetic attraction to assist the heart 10 in its natural pumping action. This technique, which does not require cutting the heart, is less invasive than previous artificial pump assisted techniques and replicates the natural pumping action of the heart. By utilizing a programmable controller 36, magnitude of the electromagnetic fields can be varied, thereby configuring the cardiac contraction force for each patient.

Moreover, the circulating blood does not leave the heart to be pumped as it does with current artificial pumps. Therefore, the potential for bleeding from the connecting in flow and out flow sites with current artificial pumps is eliminated. There is also less likelihood of blood clots forming because blood does not need to be in contact with artificial pump surfaces.

Figure 7:
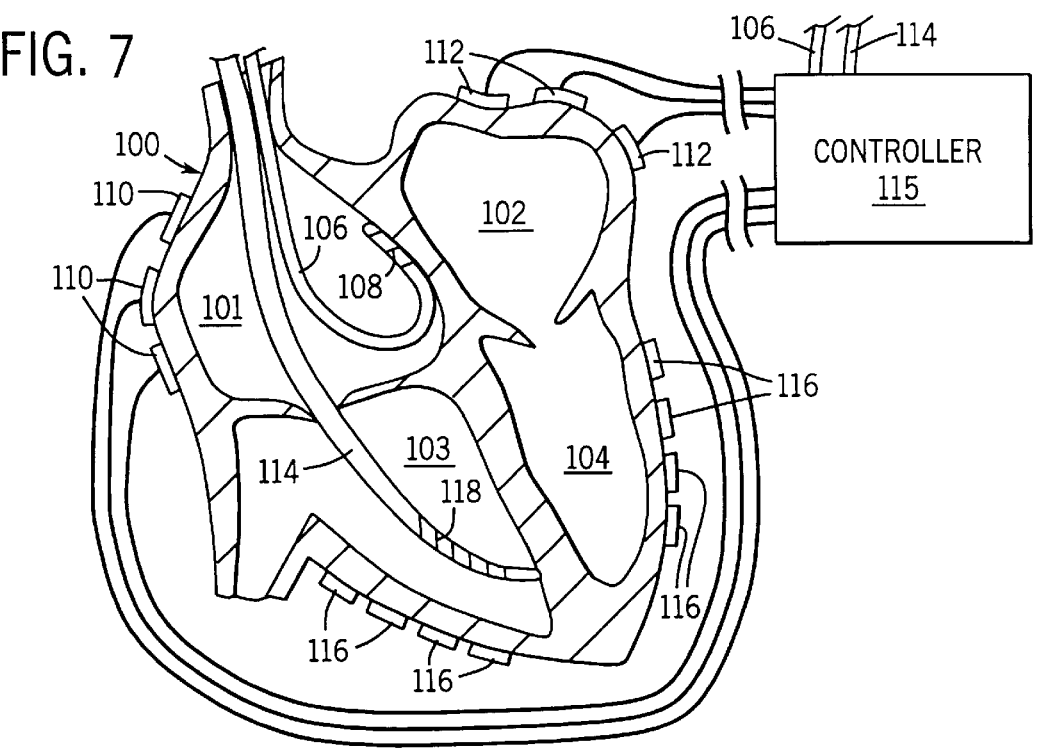
FIG. 7 is a cross-sectional view through a human heart showing another application of the present heart stimulation technique.

FIG. 7 illustrates an alternative application of the present technique for patients with atria that do not contract fully. Such a condition also may interfere with the production of electrical pulses that are conducted by the heart to the atrioventricular node to produce regular contraction of the ventricles. The lack of full atrial contraction results in loss of the primer pump action (so-called "atrial kick") and the atrial contribution to ventricular function. Loss of atrial contraction can also result in blood clot formation in the atria and subsequent emboli, e.g. embolic stroke.

To enhance the pumping action of the atria, a catheter 106 with a spiral coil 108 near its tip is positioned within the right atrium 101 against the wall of the left atrium 102. A plurality of electrical coils 110 are attached to the exterior surface of the heart 100 outside the right atrium and a second plurality of electric coils 112 are similarly applied to the exterior of the left atrium. Each of these external electric coils 110 and 112 have a structure similar to that described previously.

A conventional catheter 114, as used with cardiac pacing devices, is inserted through the right atrium 101 into the right ventricle 103 and positioned adjacent to the septum between the right and left ventricles 103 and 104. In this application of the present invention, the atrioventricular (AV) node is disabled either with pharmaceuticals or by ablation techniques. As a result, electrical signals produced for the atria do not travel to the ventricular region of the heart and conventional cardiac pacing must be employed to stimulate ventricular contractions.

A controller 115 is connected to the two catheters 106 and 114 and to the two plurality of external electrodes 110 and 112. To produce contraction of the atria 101 and 104 the pacer applies electrical pulses to the electrical coil 108 within catheter 106 and to each of the external electrical coils 110 and 112. The electrical currents applied to these coils create electromagnetic fields which result in contraction of the right and/or left atria in a manner similar to that previously described with respect to the ventricles in the FIG. 1 embodiment. By producing the electrical pulses at regular intervals, normal atrium contractions can be produced, and timed to augment ventricular function.

Because the AV node has been disabled the contractions of the atria do not produce the normal contractions of the ventricles 103 and 104. Instead, the controller 115 applies a conventional pacing pulse to the tip of the ventricular catheter 114 which stimulates the muscles of the heart to contract the ventricles and pump blood therefrom. The controller 115 times the atrial and ventricular contractions to replicate those of a normal heart, i.e. electromagnetic contraction of the atria can be specifically timed to precede the stimulation of the ventricles.

As the pumping force of the atria 101 and 102 is significantly less than that required for the ventricles 103 and 104. The use of an internal catheter 106 may not be required in all situations. As a consequence the atria pumping action may be achieved by merely the sets of external coils 110 and 112 and creating the properly poled magnetic fields from those coils to cause contraction of both atria.

Because the pumping of the ventricles 103 and 104 utilizes the normal muscle contraction of the heart in this latter embodiment, it is possible to produce some of the electrical power required by the controller 115 from the ventricular contractions. For this purpose a plurality of permanent magnets 116 can be attached to the exterior surface of the heart adjacent the right and left ventricles 103 and 104. In this enhancement, the ventricular catheter 114 has an additional electrical coil 118 adjacent its tip. As the normal ventricle contraction occurs the permanent magnets 116 move with respect to the catheter coil 118. The movement of the electric field produced by the permanent magnets with respect to the catheter coil 118 will generate an electrical current which can be utilized by the controller 115 to power the atrial stimulation.

The foregoing description is directed primarily to preferred embodiments of the invention. Although some attention was given to various alternatives within the scope of the invention, it is anticipated that skilled artisans will likely realize additional alternatives that are now apparent from the disclosure of those embodiments. Accordingly, the scope of the invention should be determined from the following claims and not limited by the above disclosure.

I claim:

1. A method for artificially contracting a heart to pump blood, that method comprising steps of:
    positioning a first magnet on one side of a first chamber of the heart, wherein the first magnet produces a first magnetic field;
    placing a second magnet on another side of the first chamber of the heart, wherein the second magnet produces a second magnetic field; and
    selectively activating the first magnet to produce the first magnetic field which interacts with the second magnetic field to contract the first chamber of the heart.

2. The method as recited in claim 1 wherein the first magnet is an electromagnet and the step of selectively activating the first magnet comprising applying electric current to the electromagnet to produce the first magnetic field.

3. The method as recited in claim 2 wherein the second magnet is an electromagnet; and further comprising applying electric current to the second magnet to produce the second magnetic field.

4. The method as recited in claim 1 wherein the step of positioning a first magnet comprises inserting a catheter, to which the first magnet is attached, into a chamber of the heart and attaching the catheter to a wall of the heart.

5. The method as recited in claim 1 wherein the step of positioning a first magnet comprises inserting a catheter, to which the first magnet is attached, into a chamber of the heart.

6. The method as recited in claim 5 wherein the step of positioning a second magnet comprises attaching the second magnet to an external surface of the heart.

7. The method as recited in claim 5 further comprising positioning a third magnet on a side of a second chamber of the heart, wherein the third magnet produces a third magnetic field which interacts with the first magnetic field to contract the second chamber of the heart.

8. The method as recited in claim 1 further comprising positioning an electrode adjacent to the heart; and selectively applying electric current to the electrode which stimulates the heart to contract a chamber of the heart other than the first chamber.

9. The method as recited in claim 1 further comprising sensing a naturally occurring contraction of the heart; and wherein selectively activating the first magnet occurs in response to sensing a naturally occurring contraction of the heart.

10. A method for artificially contracting a heart to pump blood, wherein the heart has at least first and second chambers, that method comprising steps of:

positioning a first electromagnet adjacent to the heart outside the first chamber to produce a first magnetic field;

positioning a second electromagnet adjacent to the heart outside the second chamber to produce a second magnetic field;

implanting a third electromagnet inside one of the first and second chambers to produce a third magnetic field; and selectively applying electric currents to the first, second and third electromagnets to produce the first, second and third magnetic fields which interact to contract the first and second chambers of the heart.

11. The method as recited in claim 10 further comprising varying the electric currents to control magnitudes of the first, second and third magnetic fields and thereby control contraction of the first and second chambers of the heart.

12. The method as recited in claim 11 further comprising sensing pressure in a chamber of the heart and wherein the step of varying the electric currents is responsive to that pressure.

13. The method as recited in claim 11 wherein the first chamber is the right ventricle; and the second chamber is the left ventricle.

14. A method for artificially contracting a heart to pump blood, that method comprising steps of:

attaching, a first electromagnet to a wall of the heart outside a right atrium, wherein the first electromagnet produces a first magnetic field, attaching a second electromagnet to a wall of the heart outside a left atrium of the heart, wherein the second electromagnet produces a second magnetic field; and selectively applying electric currents to the first and second electromagnets to produce the first and second magnetic fields which generate forces that contract the right and left atria.

15. The method as recited in claim 14 further comprising inserting a catheter, to which a magnet is attached, into one of the right atrium and the left atrium.

16. The method as recited in claim 14 further comprising inserting a catheter, to which a third electromagnet is attached, into one of the right atrium and the left atrium; attaching the catheter to a wall of the heart; and selectively applying an electric current to the third electromagnet to produce a third magnetic field which interacts with the first and second magnetic fields to contract the right and left atria.

17. The method as recited in claim 14 further comprising attaching an electrode to the heart; and selectively applying electric current to the electrode which stimulates the heart to contract right and left ventricles of the heart.

18. The method as recited in claim 14 further comprising implanting an electrode in one of the right and left ventricles of the heart; and selectively applying electric current to the electrode which stimulates the heart to contract the right and left ventricles.

19. The method as recited in claim 14 further comprising inserting an electric coil into one of the right and left ventricles; and attaching at least one permanent magnet to the heart to generate an electric current in the electric coil as the right and left ventricles contract.

20. An apparatus for artificially contracting a heart to pump blood, that apparatus comprising:

a first magnet on one side of a first chamber of the heart, wherein the first magnet produces a first magnetic field;

a second magnet on another side of the first chamber of the heart, wherein the second magnet produces a second magnetic field; and a controller connected to the first and second magnets and selectively activating the first magnet to produce the first magnetic field which interacts with the second magnetic field to contract the first chamber of the heart.

21. The apparatus recited in claim 20 wherein the first magnet is as electromagnet; and the controller activates the first magnet by applying electric current thereto.

22. The apparatus recited in claim 21 wherein the second magnet is an electromagnet; and the controller activates the second magnet by applying electric current thereto.

23. The apparatus as recited in claim 20 wherein the first magnet is carried by a catheter inserted into a chamber of the heart.

24. The apparatus recited in claim 23 further comprising a third magnet on a side of a second chamber of the heart, wherein the third magnet produces a third magnetic field which interacts with the first magnetic field to contract the second chamber of the heart.

25. The apparatus as recited in claim 24 wherein the third magnet is an electromagnet; and the controller activates the third magnet by applying electric current thereto.

26. A method for artificially contracting a heart to pump blood, that method comprising steps of:

positioning a first electromagnet on one side of a first chamber of the heart, wherein application of electric current to the first electromagnet produces a magnetic field;

placing a first member on another side of the first chamber of the heart, wherein the first member is attracted toward the first electromagnet by the magnetic field; and selectively applying electric current to the first electromagnet to produce the magnetic field thereby attracting the first member and contracting the first chamber of the heart.

27. The method as recited in claim 26 wherein the member is a second electromagnet; and further comprising applying another electric current to the second electromagnet to produce another magnetic field.

28. The method as recited in claim 26 wherein the member is a permanent magnet.

29. The method as recited in claim 26 wherein the step of positioning a first electromagnet comprises inserting a catheter, to which the first electromagnet is attached, into a chamber of the heart.

30. The method as recited in claim 26 further comprising positioning a second member on a side of a second chamber of the heart, wherein the second member is attracted toward the first electromagnet by the magnetic field.

31. The method as recited in claim 26 further comprising sensing a naturally occurring contraction of the heart; and wherein selectively applying electric current to the first electromagnet occurs in response to sensing a naturally occurring contraction of the heart.

* * * * *